(12) United States Patent
Pechstedt

(10) Patent No.: US 9,766,178 B2
(45) Date of Patent: Sep. 19, 2017

(54) OPTICAL SENSOR

(71) Applicant: OXSENSIS LTD, Chilton, Didcot (GB)

(72) Inventor: Ralf-Dieter Pechstedt, Didcot (GB)

(73) Assignee: Oxsensis Limited, Didcot (GB)

( * ) Notice: Subject to any disclaimer, the term of this patent is extended or adjusted under 35 U.S.C. 154(b) by 0 days.

(21) Appl. No.: 14/408,939

(22) PCT Filed: May 28, 2013

(86) PCT No.: PCT/GB2013/051396
§ 371 (c)(1),
(2) Date: Dec. 17, 2014

(87) PCT Pub. No.: WO2014/001753
PCT Pub. Date: Jan. 3, 2014

(65) Prior Publication Data
US 2015/0177132 A1 Jun. 25, 2015

(30) Foreign Application Priority Data
Jun. 27, 2012 (GB) .................... 1211407.0

(51) Int. Cl.
*G01N 21/41* (2006.01)
*G01N 21/45* (2006.01)
(Continued)

(52) U.S. Cl.
CPC ........... *G01N 21/45* (2013.01); *G01F 23/292* (2013.01); *G01K 11/3206* (2013.01);
(Continued)

(58) Field of Classification Search
CPC .... G01N 21/45; G01N 21/41; G01N 33/0004; G01N 33/18; G01N 33/22; G01F 23/292;
(Continued)

(56) References Cited

U.S. PATENT DOCUMENTS 5,207,099 A 5/1993 Baker
5,534,708 A 7/1996 Ellinger et al.
(Continued)

FOREIGN PATENT DOCUMENTS

JP 60004844 A 1/1985
WO 95/09356 A1 4/1995
(Continued)

OTHER PUBLICATIONS

Chih-Wei Lai et al.: "Application of Fabry- Perot and fiber Bragg grating pressure sensors to simultaneous measurement of liquid level and specific gravity", Measurement, vol. 45, No. 3, Apr. 1, 2012 (Apr. 1, 2012 ), pp. 469-473.
(Continued)

*Primary Examiner* — Tarifur Chowdhury
*Assistant Examiner* — Jonathon Cook
(74) *Attorney, Agent, or Firm* — Wolf, Greenfield & Sacks, P.C.

(57) ABSTRACT

An optical sensor is described for distinguishing between liquids of different refractive index, through strength of interference caused by an optical cavity having an exposed optical boundary in contact with such liquids. The sensor may be used, for example, to distinguish between water and aviation fuel in an aircraft fuel tank.

32 Claims, 12 Drawing Sheets

(51) Int. Cl.
*G01K 11/32* (2006.01)
*G01F 23/292* (2006.01)
*G01L 9/00* (2006.01)
*G01L 11/02* (2006.01)
*G01N 33/00* (2006.01)
*G01N 33/18* (2006.01)
*G01N 33/22* (2006.01)

(52) U.S. Cl.
CPC ............ *G01L 9/0079* (2013.01); *G01L 11/02* (2013.01); *G01N 33/0004* (2013.01); *G01N 33/18* (2013.01); *G01N 33/22* (2013.01)

(58) Field of Classification Search
CPC ... G01K 11/3206; G01L 9/0079; G01L 11/02; G01J 3/02; G01J 3/26; G01B 9/02027
USPC .................................................. 356/454, 517
See application file for complete search history.

(56) References Cited

U.S. PATENT DOCUMENTS

| | | |
|---|---|---|
| 6,069,686 A | 5/2000 | Wang et al. |
| 2003/0030790 A1 | 2/2003 | Rakucewicz |
| 2003/0112443 A1* | 6/2003 | Hjelme .................. G01N 21/45 356/480 |
| 2005/0046862 A1* | 3/2005 | Melnyk .............. G01D 5/35303 356/480 |
| 2007/0006663 A1 | 1/2007 | Zerwekh et al. |
| 2011/0110621 A1* | 5/2011 | Duncan .................. E21B 47/06 385/13 |
| 2011/0172959 A1 | 7/2011 | Childers et al. |
| 2011/0190640 A1 | 8/2011 | Bremer et al. |
| 2011/0264398 A1 | 10/2011 | Niewczas et al. |

FOREIGN PATENT DOCUMENTS

| | | |
|---|---|---|
| WO | 99/60341 A1 | 11/1999 |
| WO | 2009077727 A2 | 6/2009 |
| WO | 2013/136071 A2 | 9/2013 |
| WO | 2013/136072 A1 | 9/2013 |
| WO | WO 2013/139783 A1 | 9/2013 |

OTHER PUBLICATIONS

United Kingdsom International Search Report and Written Opinion from corresponding PCT/GB2013/051396 dated Oct. 4, 2013.
Liu T. et al.: A frequency division multiplexed low-finesse fiber optic Fabry-Perot sensor system for strain and displacement meaurements, Rev. Sci. Instr., vol. 71, 1275 (2000).
Lu T. et al.: "Extrinsic Fabry- Perot Cavity Optical Fiber Liquid-Level Sensor", Applied Optics, Optical Society of America, Washington, DC; US, vol. 46, No. 18, Jun. 20, 2007 (Jun. 20, 2007), pp. 3682-3687.
Qingxu Yu et al.: "Pressure sensor based on the fiber-optic extrinsic Fabry- Perot interferometer", Photonic Sensors, vol. 1, No. 1, Nov. 22, 2010 (Nov. 22, 2010), pp. 72-83.
Rao Y-J.: In-fibre Bragg grating sensors Meas. Sci Technol., vol. 8, 355-375 (1997).
Shinpaugh et al.: Signal-processing techniques for low signal-to-noise ratio laser Doppler velocimetry signals, Experiments in Fluids, vol. 12, 319-328 (1992).
Zhao Jiang-Hai et al.: "White-Light Interferometric Fiber Optic Liquid Level Sensor Based on MEMS Fabry-Perot Cavity", Photonics and Optoelectronic (SOPO), 2010 Symposium on, IEEE, Piscataway, NJ, USA, Jun. 19, 2010 (Jun. 19, 2010), pp. 1-4.
Zhenguo J. et al.: White light optical fiber EFPI sensor based on cross-correlation signal processing method, Proc. 6th International Symposium on Test and Measurement. Dalian, China, Jun. 1-4, 2005, vol. 4, 3509 (2005).

* cited by examiner

OPTICAL SENSOR

This application is the U.S. National Phase Application under 35 U.S.C. §371 of International Application No. PCT/GB2013/051396, filed May 28, 2013, which claims priority to United Kingdom Patent Application No. GB1211407.0, filed Jun. 27, 2012. These prior applications are incorporated by reference herein in their entirety.

The present invention relates to an optical sensor, for example to such a sensor which can be used to distinguish between contact with materials of different refractive index. Such a sensor may be used, for example, to distinguish between contact with a gas and with a liquid, and optionally between one or more different such liquids such as between aviation fuel and/or water in an aircraft fuel tank. The optical sensor may also sense other parameters such as temperature and pressure.

INTRODUCTION

Optical sensors for sensing the presence, identities and/or properties of liquids are used in a variety of applications. One such application is in aircraft fuel systems for monitoring the level or mass of fuel in a tank. The use of optical sensors rather than electrical sensors can greatly enhance safety in this and other applications where explosion is a risk.

U.S. Pat. No. 5,207,099 describes an aircraft fuel gauging system using optical pressure sensors mounted in a fuel tank. The output from each sensor is used to determine the mass of fuel above the sensor, so that the mass of fuel in the tank can be derived. Some different ways in which the optical pressure sensors can be implemented are described, including having a diaphragm deflected by pressure which interacts with an optical beam, direct sensors in which force applied to an optical element directly alters its transmission, polarisation or other measurable characteristic, displacement induced micro-bending sensors in which micro-bending along the axis of an optical fibre introduces extra losses caused by mode coupling from the core to the cladding of the optical fibre, and displacement induced birefringence sensors in which external force causes stress in a fibre thus altering the refractive index difference between two birefringence modes.

Water can separate out from fuel in aircraft fuel systems to form distinct layers in the fuel tank, and it may therefore be desirable for an optical sensor to distinguish between such layers of water and aviation fuel, and to be able to distinguish between such layers of liquid and air or vapour phases in the tank. Such an optical sensor is described in U.S. Pat. No. 5,534,708, which describes the use of a prism having a conical tip. Whether probe light transmitted along the prism is reflected back to a sensor or escapes through the tip depends on the difference in refractive index between the material of prism and the refractive index of the air, aviation fuel or water in contact with the conical tip. To separately detect the presence of either water or aviation fuel, two separate prisms with different internal reflection angles at the tip are used.

Optical sensors for detecting liquids may be used in a variety of other applications.

It would be desirable to address problems and limitations of the related prior art.

SUMMARY OF THE INVENTION

The invention provides an optical sensor which can be used to provide an indication of a liquid to be sensed. This indication is based on the strength of detected interference at a sensor head. The sensor head may be arranged such that the strength of the detected interference depends on or is indicative of the refractive index of the liquid to be sensed.

Such an optical sensor may also or instead be used to provide other indications of the state of a boundary between the sensor head and an environment, for example detecting sooty or other deposits, degradation or etching or other changes to the boundary through detection of the strength of the detected interference.

The invention also provides such an optical sensor which can be used to determine one or more other parameters at the sensor head, such as temperature and pressure, and to such an optical sensor which can provide an indication of the state of a boundary such as refractive index or another indication of a liquid to be sensed as well as pressure and temperature simultaneously. Pressure parameters may include static or low frequency variations in pressure, or higher frequency variations such as acoustic signals.

Accordingly, the invention provides an optical sensor comprising: a sensor head having one or more optical cavities, such as Fabry Perot cavities, including a first optical cavity arranged to have an external boundary; an optical source arranged to deliver probe light to the one or more optical cavities; a detector arranged to receive said probe light from the one or more optical cavities and to detect interference in said probe light caused by at least the first optical cavity; and an analyser arranged to generate an indication of the state of the external boundary based on a strength of the detected interference caused by the first optical cavity. The state of the boundary may for example be or be related to or be based on reflectivity to said probe light at the boundary. One aspect of such a state could be reflectivity due to the presence, absence or identity of a liquid in contact with the boundary, and the indication may then be an indication of the liquid to be sensed, for example responsive to the refractive index of the liquid.

The optical source is arranged to deliver probe light across a spread spectrum or range of wavelengths so that the strength of interference due to a particular optical cavity can be detected, for example using one or more super luminescent diodes or another broadband source, or using one or more tunable lasers swept or chirped across a frequency band. Typically, a bandwidth of 30 nm or more may be appropriate. The sensor head may conveniently be coupled to the optical source and the detector using an optical fibre carrying said probe light.

The one or more optical cavities may include one or more further optical cavities in addition to the first optical cavity, and the detector may then be arranged to make a different detection of interference, for example a detection of the strength of the interference in said received probe light, in respect of each of the further optical cavities.

At least one of said further optical cavities may be a pressure sensing physical cavity in the sensor head, and the analyser may then be arranged to generate an indication of pressure at said sensor head from the effect of changes in optical path difference of said pressure sensing cavity under changes in pressure on the detected interference in said received probe light caused by the pressure sensing cavity. Such an indication may also be corrected for changes in the optical path difference of said pressure sensing cavity due to changes in temperature at said sensor head.

At least one of said optical cavities (but preferably not the pressure sensing cavity) may be a temperature sensing optical cavity, and the analyser may be arranged to generate an indication of temperature at said sensor head from the effect of changes in optical path difference of said temperature sensing optical cavity under changes in temperature on the detected interference in said received probe light caused by the temperature sensing optical cavity, and/or to correct an above mentioned indication of pressure based on said indication of temperature.

The analyser may be arranged to generate the indication of the liquid to be sensed based on relative strengths of the detected interference in said received probe light caused by two or more of the optical cavities respectively.

The optical sensor may further, or instead of said temperature sensing optical cavity, comprise an optical fibre arranged to deliver said probe light to the sensor head, the optical fibre having formed therein proximal to the sensor head a Bragg grating, the optical sensor being arranged to detect variations in temperature at the sensor head from variations in a spectral characteristic of the Bragg grating, for example from variations in the Bragg wavelength. The Bragg grating may be interrogated using the probe light, for example using a waveband of the probe light not used for detecting interference in the one or more optical cavities of the sensor head.

Various materials sufficiently transparent to the probe light may be used to form one or more of the optical cavities, such as sapphire, silicon and silica glass. Such materials may for example be selected based on refractive index relative to one or more liquids to be sensed, for resistance to environmental degradation in the required applications, and so forth.

The detector may comprise apparatus arranged to detect in said received probe light an interference spectrum caused by the one or more optical cavities in the sensor head, which apparatus may be referred to herein as a spectral engine; and a transform function arranged to generate an optical path difference signal representing the strength of the detected interference for at least one or more optical path differences corresponding to said one or more optical cavities.

The transform function may be arranged to generate said optical path difference signal from said interference spectrum using one of: a discrete Fourier transform; and a cross-correlation of the interference spectrum with a set of periodic transfer functions. Other techniques may be used. The discrete Fourier transform may be a fast Fourier transform. The strength of detected interference caused by any of the optical cavities may be determined from a height of a corresponding peak in the optical path difference signal, or from some other aspect of the signal such as the area under a peak or under some part of a peak.

A measure of optical path difference of one or more of the optical cavities at the sensor head may also be determined from the interference spectrum of the received probe light, for example from the optical path difference signal as mentioned above, and can then be used to determine a parameter at the sensor head. For example, an indication of pressure at the sensor head may be generated from changes in optical path difference at a pressure sensing optical cavity of said sensor head, and/or an indication of temperature at the sensor head may be generated from changes in optical path difference at a temperature sensing optical cavity, the changes in optical path difference being determined from said optical path difference signal, for example from changes in position of a peak corresponding to an optical cavity in the sensor head The invention also provides an aircraft fuel system comprising an optical sensor as set out herein installed in a fuel tank of the aircraft fuel system, in which case the indication of a liquid which the analyser is arranged to generate may distinguish between water, fuel and gas (which may include air, water vapour, fuel vapour, injected nitrogen ullage gas and similar) found at any one time at the boundary of the first optical cavity. The analyser may be further arranged to generate an indication of at least one of temperature and pressure at the sensor head by interrogation of one or more of said optical cavities using said probe light.

The invention also provides methods corresponding to the above apparatus, such as a method of sensing, comprising: providing a sensor head comprising at least a first optical cavity having an optical boundary exposed to an environment; and detecting reflection strength at the exposed optical boundary from strength of interference caused by the first optical cavity in probe light, for example spread spectrum or broadband probe light, delivered to and received back from the sensor head. This may be, for example, a method of sensing a liquid in contact with the exposed optical boundary, further comprising generating an indication of the liquid to be sensed from the strength of said interference, or may be a method of sensing solid deposits on the exposed optical boundary, further comprising generating an indication of the solid deposits to be sensed from the strength of said interference.

The strength of the interference may be used as an indicator or measure of refractive index of a liquid in contact with the exposed optical boundary, and may thereby be used to distinguish between different liquids having different refractive indices.

BRIEF SUMMARY OF THE DRAWINGS

Embodiments of the invention will now be described, by way of example only, with reference to the accompanying drawings of which.

DETAILED DESCRIPTION OF EMBODIMENTS

Figure 1:
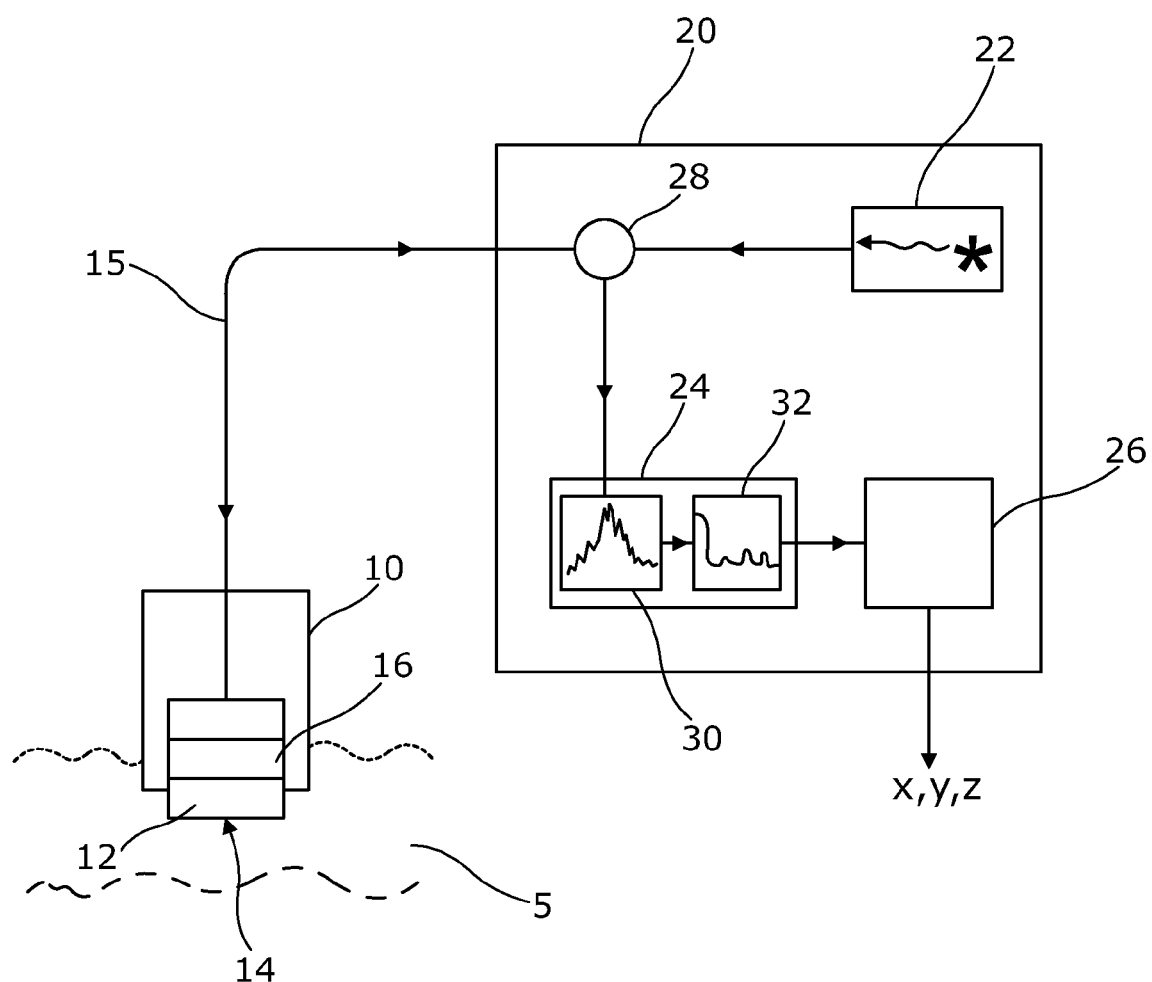
FIG. 1 schematically shows a sensor according to the invention.

FIG. 1 illustrates schematically an optical sensor for sensing a liquid 5 comprising a sensor head 10 and an interrogator 20 optically coupled to the sensor head by one or more optical fibres 15. The sensor head 10 includes at least a first optical cavity 12 arranged such that a liquid to be sensed may contact an optical boundary 14 of the first optical cavity 12. The interrogator 20 includes an optical source 22 arranged to deliver probe light to the first optical cavity 12, a detector 24 arranged to receive probe light from the first optical cavity 12 and to detect interference in the probe light resulting from the first optical cavity, and an analyser 26 arranged to generate an indication x of the liquid to be sensed from a strength or magnitude of the detected interference due to the first optical cavity. The indication x of the liquid may be, for example, an indication of the presence or absence of a liquid, an identification of a particular liquid such as aviation fuel or water or absence of any such liquid, and/or a measure of a property of a detected liquid such as a refractive index of the liquid. The optical sensor may also use detected interference properties of the probe light resulting from the first optical cavity to generate an indication of one or more other parameters at the sensor head such as temperature.

The sensor head 10 may include one or more further optical cavities 16 which are also interrogated by the interrogator using probe light. These one or more further optical cavities may be used for a variety of purposes as described in more detail below including for determining the relative strength of the interference in the probe light resulting from the first optical cavity, and/or for determining one or more other parameters at the sensor head 10 such as temperature and/or pressure. Such other parameters, whether derived from interference from either or both of the first and further optical cavities are generally denoted in FIG. 1 as y, z.

The interrogator 20 includes a coupler 28 for coupling both the optical source 22 and the detector 24 to the sensor head 10. The optical source 22 may be provided, for example, by one or more super-luminescent diodes providing broad band probe light, or by one or more swept frequency laser sources, so that the sensor head 10 can be interrogated by the interrogator using white light or broad band interferometry techniques, for example similar to those discussed in WO99/60341. To this end, the detector 24 includes a spectral engine 30 arranged to detect in the received probe light, across a range of wavelength of the optical source 22, an interference spectrum caused by the one or more optical cavities in the sensor head, and a transform function 32 arranged to generate an optical path difference signal representing the contribution of each optical cavity to the interference spectrum as a function of optical path difference. As an alternative, interference properties of the one or more optical cavities could be detected using one or more sensing interferometers for example as described in WO99/60341.

Figure 3:
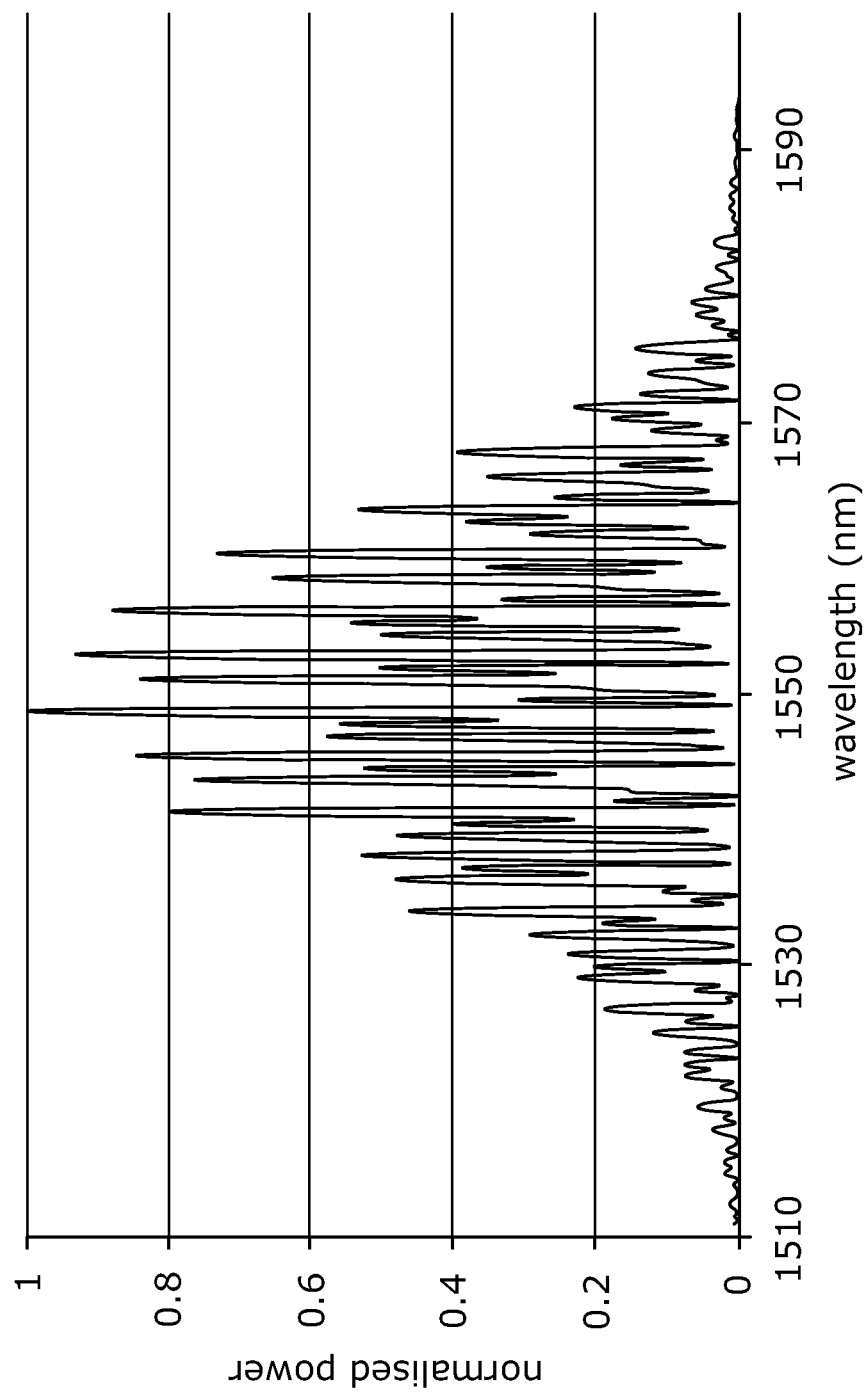
FIG. 3 is an interference spectrum in probe light received back from the sensor head.

The spectral engine 30 may be implemented in various ways. If a broadband optical source 22 such as one or more super luminescent diodes is used then the spectral engine could be implemented using a dispersive optical element in conjunction with a CCD array. If a swept optical source such as a tuneable laser is used then the spectral engine could use a photodiode detector with suitable timing of data collection relative to the wavelength sweeping of the optical source. The transform function 32 may be implemented for example using a discrete Fourier transform such as a fast Fourier transform of the interference spectrum, or using a cross correlation of the interference spectrum with a set of periodic transfer functions corresponding to a set of optical path differences. Use of a fast Fourier transform to generate a suitable optical path difference signal representing one or more optical cavities is discussed in Liu and Fernando, Review of Scientific Instruments, Volume 71, number 3, March 2000. The equivalent use of a cross correlation function is discussed in Zhenguo and Qingxu, Proceedings of the sixth International Symposium on Test and Measurement, Dalian, China, 1-4 Jun. 2005, volume 4, page 3509, 2005, from which it can be seen that suitable cross correlation can be carried out using the following equations:

$$T(OPD, \lambda) = 1 - \cos\left(\frac{2\pi OPD}{\lambda}\right) \quad \text{(eqn 1)}$$

$$CCF(OPD) = \sum_{i=0}^{N-1} A_i T(OPD, \lambda_i) = \sum_{i=0}^{N-1} A_i \left\{1 - \cos\left(\frac{2\pi OPD}{\lambda_i}\right)\right\} \quad \text{(eqn 2)}$$

where T is a periodic transfer function corresponding to a particular optical path difference OPD at each wavelength $\lambda$ of the probe light, CCF is the cross correlation function and $A_i$ is the amplitude of the interference spectrum at each wavelength $\lambda_i$ for a range of interference spectrum pixel elements i=0 to N−1 for example as shown in FIG. 3 discussed below.

Figure 2:
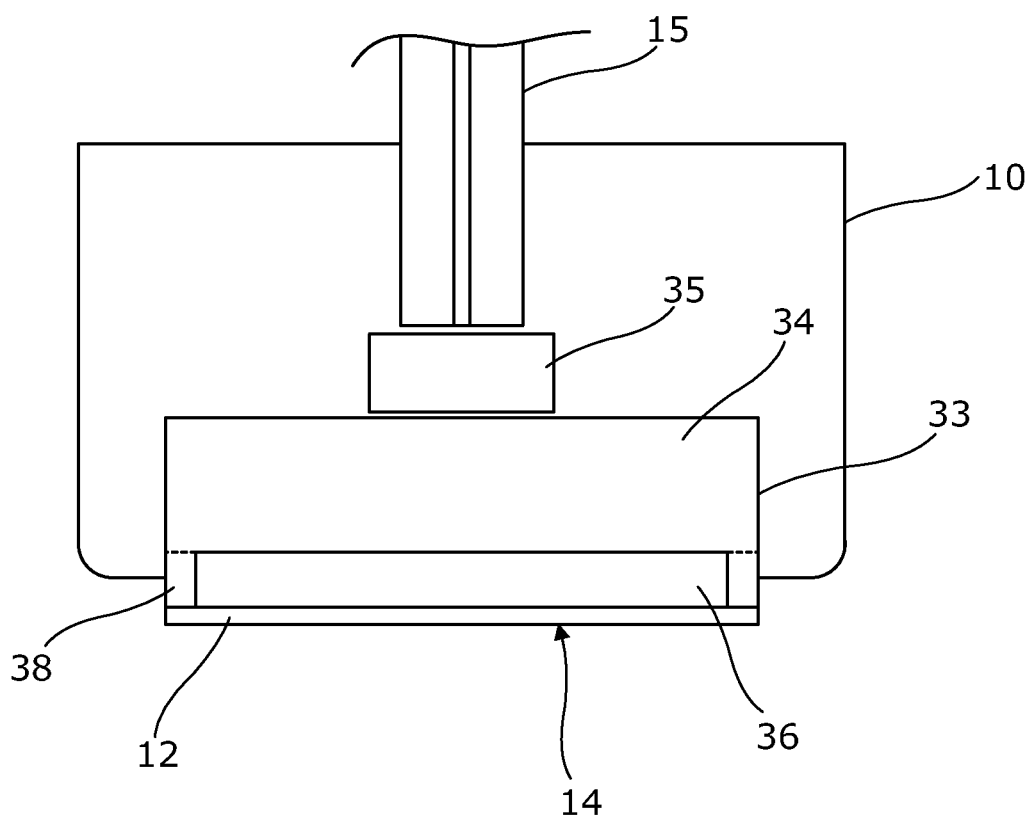
FIG. 2 shows in more detail a cross section of the sensor head of FIG. 1.

FIG. 2 illustrates schematically in cross section a way in which the sensor head 10 may be implemented. Optical fibre 15 coupling the sensor head to the interrogator 20 is coupled to a sensing element 33, typically using an optical coupling 35 such as a micro-lens although in some designs such an optical coupling 35 may be omitted. Suitable optical coupling techniques are discussed in WO2009/077727. Sensing element 33 comprises at least the above mentioned first optical cavity 12 which is arranged such that a liquid to be sensed contacts an optical boundary 14 of the first optical cavity 12 when the sensor head 10 is brought into contact with the liquid. The sensing element 33 may be protected from damage by a shield provided by a metal gauze, an apertured cover, or some other arrangement.

The sensing element 33 illustrated in FIG. 2 comprises two further optical cavities: a base cavity 34 and a pressure sensing cavity 36. The pressure sensing optical cavity is formed by a separation between the base optical cavity and the first optical cavity which is effected by a shoulder 38 on the outer rim of the base optical cavity 34, with the pressure sensing optical cavity being filled with a gas, for example air, which may be at a low pressure for example below atmospheric pressure if required. The base optical cavity and the first optical cavity are made of materials which are transparent to the probe light, for example using a suitable glass, ceramic or semiconductor material having a suitable refractive index.

The first optical cavity in FIG. 2 is sufficiently thin that the material of the first optical cavity acts as a diaphragm under external pressure on the sensing element 33 which thereby leads to deflection of the diaphragm and a change in the physical spacing between the base optical cavity 34 and the first optical cavity 12. A change in external pressure therefore gives rise to a change in the optical path difference of the pressure sensing cavity 36 which can be detected by the interrogator 20. For a suitably designed diaphragm, over sufficiently small deflections, the centre deflection w of the diaphragm varies in an approximately linear fashion with pressure p according to:

$$w = \frac{3(1-v^2)R^4}{16Et^3} p \quad \text{(eqn 3)}$$

where R is the diaphragm radius, E and v are the Young's modulus and Poisson's ratio of the diaphragm material, and t is the diaphragm thickness. The interrogator 20 maybe arranged to monitor variations in the optical path difference of the pressure sensing cavity 36 under such pressure induced deflections, and with suitable calibration for absolute pressure and/or variations in pressure, generate one or more indications of pressure (which could be indications of absolute pressure, variations in pressure, or a pressure related parameter such as an acoustic indication) at the sensor head 10.

The materials of the first optical cavity and the base optical cavity expand and contract and undergo changes in refractive index under changes in temperature at the sensor head, leading to corresponding changes in optical path difference of these optical cavities. Typically, such changes in optical path difference follow a monotonic function of temperature. Using suitable calibration therefore, either one or both of the changes in optical path difference of the first and base optical cavities can be used by the interrogator 20 to detect temperature at the sensor head.

Due to thermal expansion of the material of the sensor head 10 the pressure sensing cavity 36 will respond not only to pressure but also to temperature. Simultaneous determination of temperature at the sensor head can be used to compensate for this cross-sensitivity, therefore enabling the sensor head to be used more accurately for measuring absolute pressure rather than just variations or oscillations in pressure, for example using the techniques set out in GB1204674.4 and subsequent publications of this and corresponding patent applications which are hereby incorporated by reference.

It can be seen that the sensing element 33 of the sensor head 10 presents to the interrogator 20 a series of Fabry Perot cavities defined by the boundaries between the various layers and materials of the sensing element, although other designs of a sensor head and interrogator whereby other optical elements such as Mach-Zehnder or Michelson elements are implemented could be used.

FIG. 3 shows a suitably normalised interference spectrum output of the spectral engine 30 on interrogation of a sensor head 10 as illustrated in FIG. 2. The particular properties of the sensor head used for this purpose were: physical thicknesses of the first optical cavity, the pressure sensing optical cavity and the base optical cavity of 181 µm, 492 µm and 365 µm respectively; the pressure sensing cavity filled with air with a refractive index of 1.0; and the base and first optical cavities being formed of sapphire with a refractive index of 1.76. The illustrated interference spectrum comprises a superposition of three separate interference spectra generated by the individual Fabry Perot optical cavities of FIG. 2, under an envelope over the full wavelength range of about 1510 nm to 1590 nm which is representative of the probe light spectrum emitted by the optical source 22.

Figure 4:
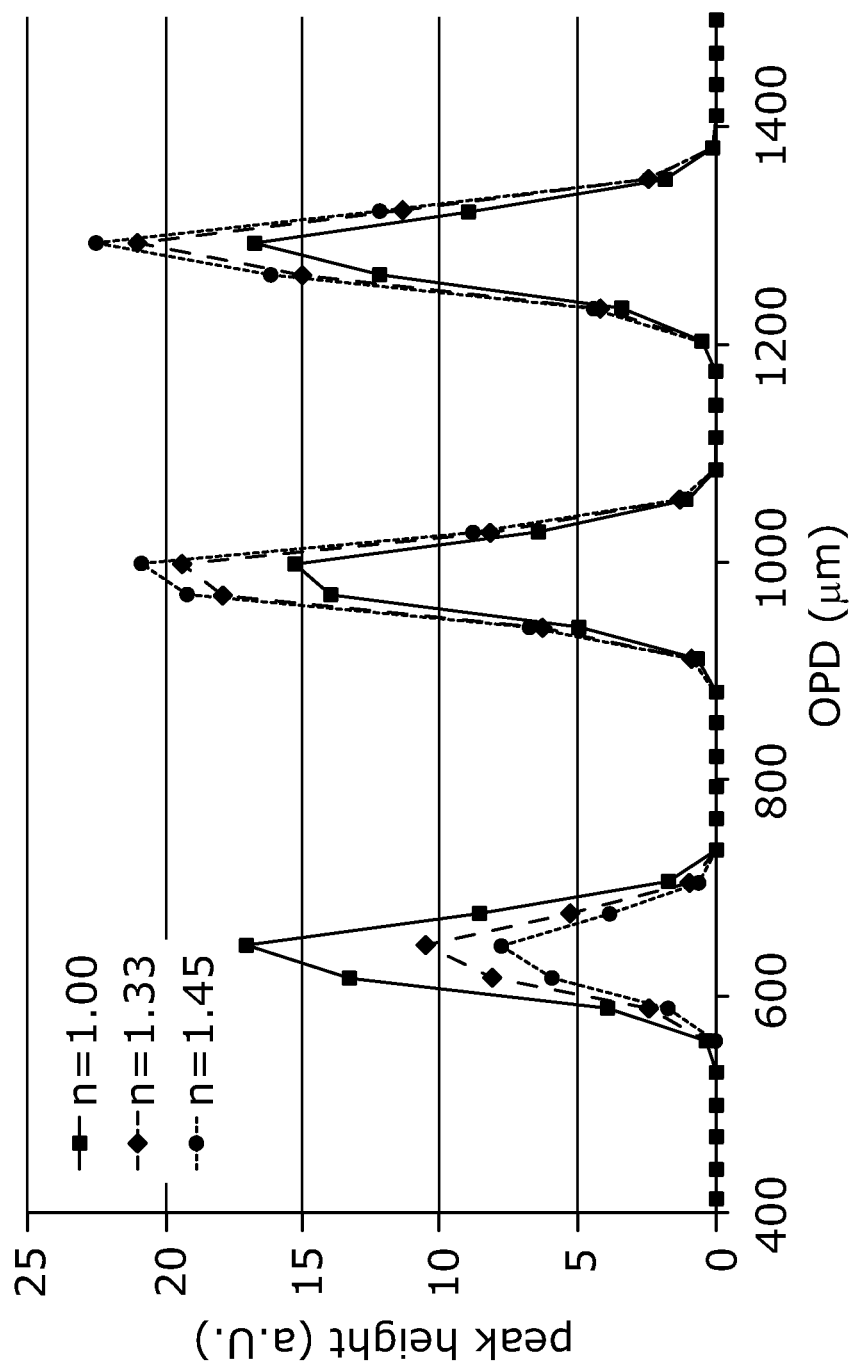
FIG. 4 presents an optical path difference signal derived from the interference spectrum of FIG. 3 using a Fourier transform, when fluids of three different refractive indices (air, water, aviation fuel) are in contact with an exposed optical boundary of the sensor head of FIG. 2.

FIG. 4 shows a fast Fourier transform of the interference spectrum of FIG. 3 plotted against optical path difference, for example which may be produced by the transform function 32 in the detector 24 of the interrogator 20 of FIG. 1. The fast Fourier transform data represents the strength of the interference in the interference spectrum as a function of optical path difference of an optical cavity which would give rise to that interference, and we therefore refer to this transformed interference spectrum as an optical path difference signal. The optical path difference signal in FIG. 4 is shown for three different values of refractive index of gas or liquid in contact with the optical boundary 14 of the first optical cavity 12 of FIG. 2. Three sets of peaks are apparent in each of the optical path difference signals, corresponding to the three optical cavities of the sensing element 33 of FIG. 2 with optical path differences of the base, pressure sensing and first optical cavities of about 1284 µm, 984 µm and 637 µm respectively. The magnitude of each of the three peaks therefore represents the strength of interference in the probe light due to each of the three optical cavities. The strength of the interference attributable to a particular optical cavity can therefore be determined for example from the height of a relevant peak or close to the peak, the area under a relevant peak, or similar. To this end, the strength of interference may be determined more accurately if desired by fitting a curve to a particular peak or carrying out similar data analysis on a suitable portion of the optical path difference signal corresponding to a particular optical cavity using techniques familiar to the person skilled in the art. Suitable curve fitting techniques are described in K. A. Shinpaugh et al., Experiments in Fluids, vol 12, 319-328 (1992). In this reference curve fitting is used to estimate a more accurate position of a peak, but applying the procedure in the present context would also increase the accuracy of determination of peak height corresponding to interference strength due to a particular optical cavity.

The strength of the interference in the probe light due to the first optical cavity depends on the strength of reflection of the probe light at the optical boundary 14 which may be in contact with a liquid to be sensed. The strength of this reflection, in turn, depends upon the relative refractive indices of the material of the first optical cavity 12 and of the liquid to be sensed, according to the ratio of the square of the difference of the refractive indices to the square of the sum of the refractive indices. On this basis, the reflection of light at an interface between sapphire and air is about 7.5%, between sapphire and water (refractive index typically about 1.33) is about 3.0%, and between sapphire and aviation fuel (refractive index typically about 1.45) is about 1.0%. This change in reflectivity is apparent in the three curves of FIG. 4. A first curve (solid) is for contact of air (n=1.0) with the optical boundary 14, a second curve (broken line) is for contact of water (n=1.33) with the optical boundary 14, and a third curve (dotted line) is for contact of aviation fuel (n=1.45) with the optical boundary 14.

From a consideration of FIG. 4, there are various ways in which the strength of the detected interference caused by the first optical cavity can be used by the analyser 26 of FIG. 1 to generate an indication of a liquid to be sensed. According to a first technique, the interference caused by the first optical cavity can be considered in isolation from interference caused by other optical cavities (which therefore need not be present in the sensor head). One or more thresholds can be provided at the analyser 26 for the interference strength, and the presence or absence of a liquid, and if required a determination of which of two or more different liquids such as aviation fuel and water are present at the optical boundary, can be decided based on where the interference strength lies in respect to the one or more thresholds, for example based on which thresholds are exceeded. Referring to FIG. 4, a peak strength (of the left hand peak which corresponds to the first optical cavity) of above 13.0 could indicate the presence of air, between 8.0 and 13.0 could indicate water, and below 8.0 could indicate aviation fuel.

Figure 5:
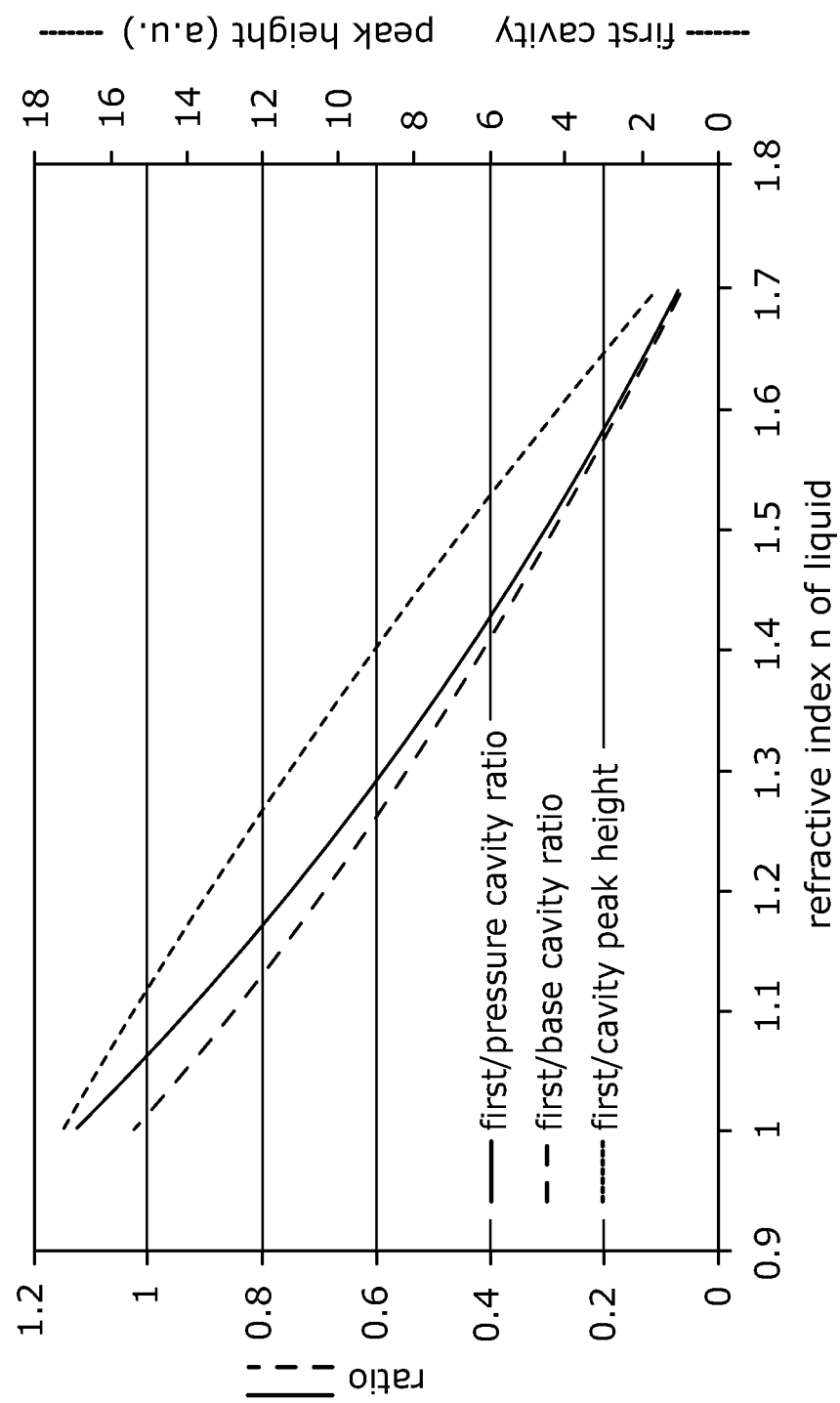
FIG. 5 presents heights and ratios of peak heights of FIG. 4 plotted against a continuous range refractive indices.

A more reliable second technique may make use of the observation that as the strength of interference of the first optical cavity decreases due to changes in refractive index at the optical boundary 14, the strength of the interference due to any further optical cavities increases. This is in contrast to changes in the intensity of the optical source, sensitivity of the detector, reduced light transmission in the optical fibre 15 and other similar effects, which tend to lead to strengths of interference due to all of the optical cavities changing in same direction. This observation may therefore be used in providing the analyser 26 with functionality to generate an indication of the liquid to be sensed based on relative strengths of detected interference in the received probe light caused by respective two or more of the optical cavities at the sensor head. Referring to FIG. 4 and FIG. 5 discussed below, a ratio of the heights of the left hand to the right hand peaks (corresponding to the first optical cavity and the base optical cavity) of above 0.75 could cause the analyser to indicate the presence of air, between 0.75 and 0.42 could cause the analyser to indicate the presence of water, and below 0.42 could cause the analyser to indicate the presence of aviation fuel. Of course, the strength of interference due to the pressure sensing optical cavity and/or any other cavities could also be used to improve the accuracy and reliability of this technique.

According to a third technique, the strength of interference due to the first optical cavity, and optionally combined with the strength of interference due to one or more other optical cavities, can be used to provide a continuous measure of refractive index for output by the analyser 26. For example, with reference to the data of FIG. 4 the refractive index of the liquid to be detected is approximately in linear relationship to the ratio of strengths of interference of the first and base optical cavities, and more sophisticated non-linear calibrations can easily be implemented by the analyser 26.

FIG. 5 shows how the ratios of the heights of the peaks in the optical path difference signal of FIG. 4 vary with refractive index of the liquid in contact with the optical boundary 14. The solid curve shows this ratio between the first optical cavity 12 and the pressure sensing optical cavity 36 of FIG. 2, and the broken curve shows this ratio between the first optical cavity 12 and the base optical cavity 34. For comparison, the simple peak height for the first optical cavity is shown over the same range of refractive index as a dotted line. Any of these or similar curves based on combinations of optical cavities or functional relationships between the strengths of interference for different optical cavities can be used to calibrate the sensor to detect refractive index, or to establish suitable thresholds for liquid detection, and to operate the sensor.

In particular embodiments of the invention, the analyser 26 may be arranged to determine and generate an output indicating which of water, aviation fuel, or gas (which may include for example air, fuel vapour, water vapour etc) is in contact with the optical boundary 14 of the sensor head 10, for example using one of the particular techniques outlined above. Typically the refractive index for aviation fuel varies between about 1.4 and 1.5 depending on the fuel type and temperature, and it can be seen from FIG. 5 that aviation fuel can easily be distinguished from water with a refractive index of 1.33 by the sensor, with corresponding changes in peak height or peak height ratio of at least 20%, and that water can easily be distinguished from gas with a refractive index of about 1.0.

Figure 6:
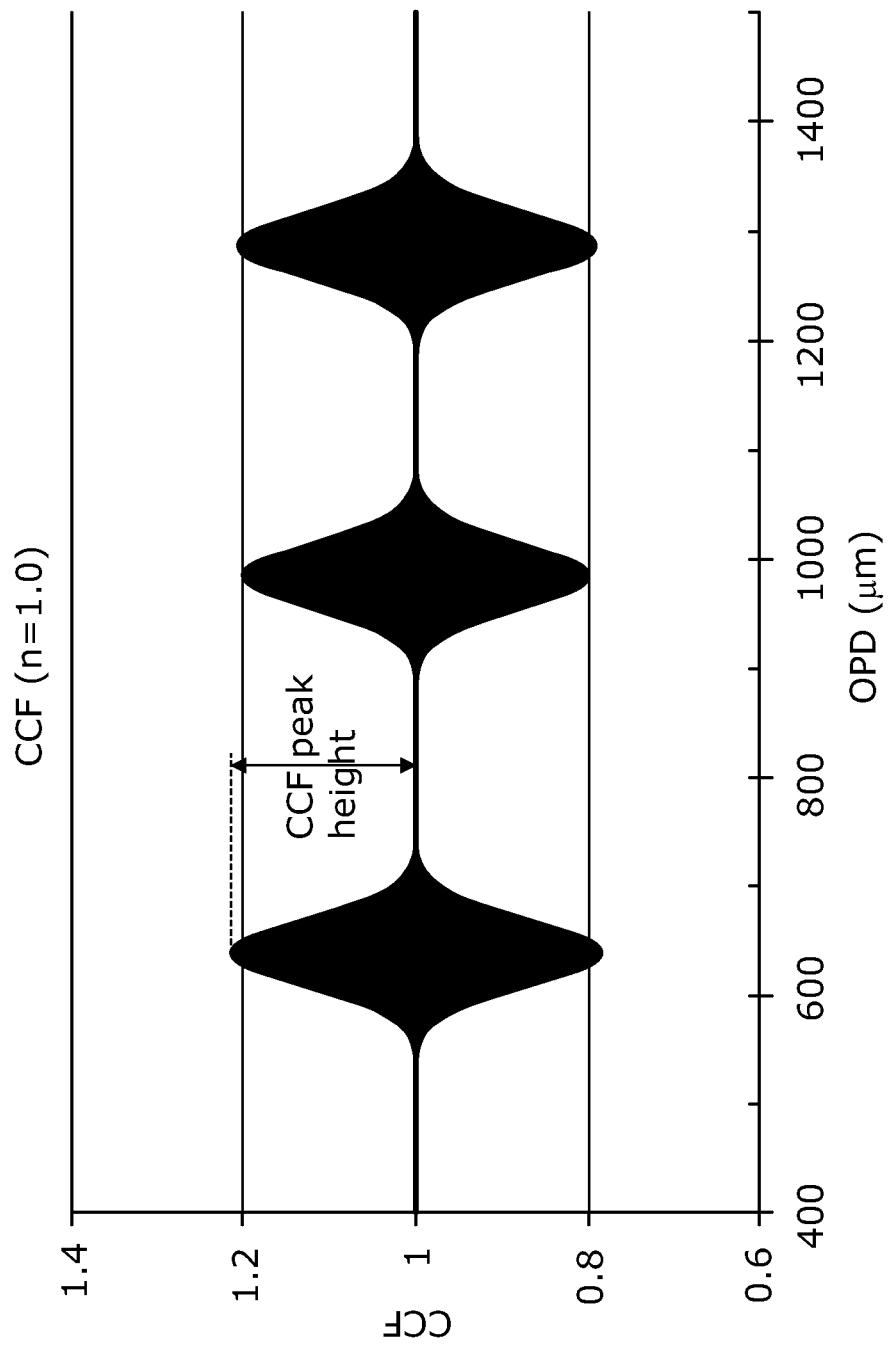
FIG. 6 is an optical path difference signal derived from the interference spectrum of FIG. 3 using a cross correlation function, when air is in contact with an exposed optical boundary of the sensor head of FIG. 2.
Figure 7:
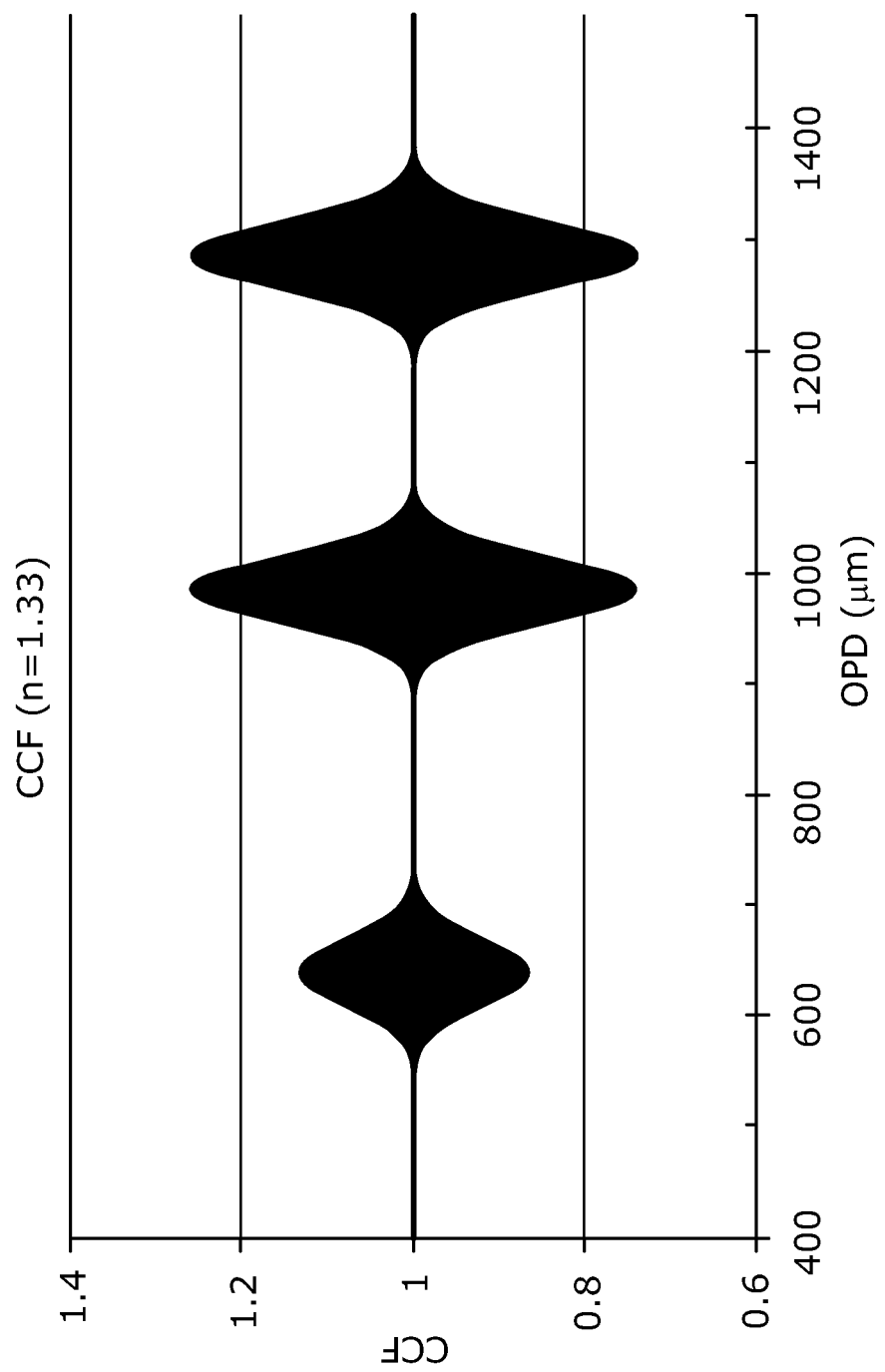
FIG. 7 is an optical path difference signal derived from the interference spectrum of FIG. 3 using a cross correlation function, when water is in contact with an exposed optical boundary of the sensor head of FIG. 2.

It has already been mentioned above that the transform function 32 of the detector 24 may be implemented using a cross correlation function scheme rather than a Fourier transform scheme. FIG. 6 shows the results of implementing the cross correlation function of equation 2 above across a range of optical path differences spanning all three optical cavities of the sensor head 10 of FIG. 2, having the same properties as were used in respect of FIGS. 3 and 4, and with the optical boundary 14 being exposed to air (n=1.0). In FIG. 6 only the envelope of the cross correlation function is visible due to the resolution of the drawing. The envelope is made up of much more rapid oscillations of the cross correlation function which are not visible in FIG. 6. The similarities between the cross correlation function of FIG. 6 and the fast Fourier transform function of FIG. 4 are self evident, with the height or size of the peaks from left to right in the figure representing the strength of interference in the received probe light due to each of the first, pressure sensing and base optical cavities respectively. The results of immersing the same sensor head 10 in water (n=1.33) are shown in FIG. 7. In correspondence with the behaviour observed in FIG. 4, the cross correlation function peak representing the first optical cavity has reduced in height, and the peaks representing the other optical cavities have increased in height. The peaks of the cross correlation function can therefore be used to infer strength of the interference due to one or more of the optical cavities, and thereby generate an indication of the liquid to be sensed in the same way as described above in respect of the detector 24 when implemented using a Fourier transform or similar.

Figure 8:
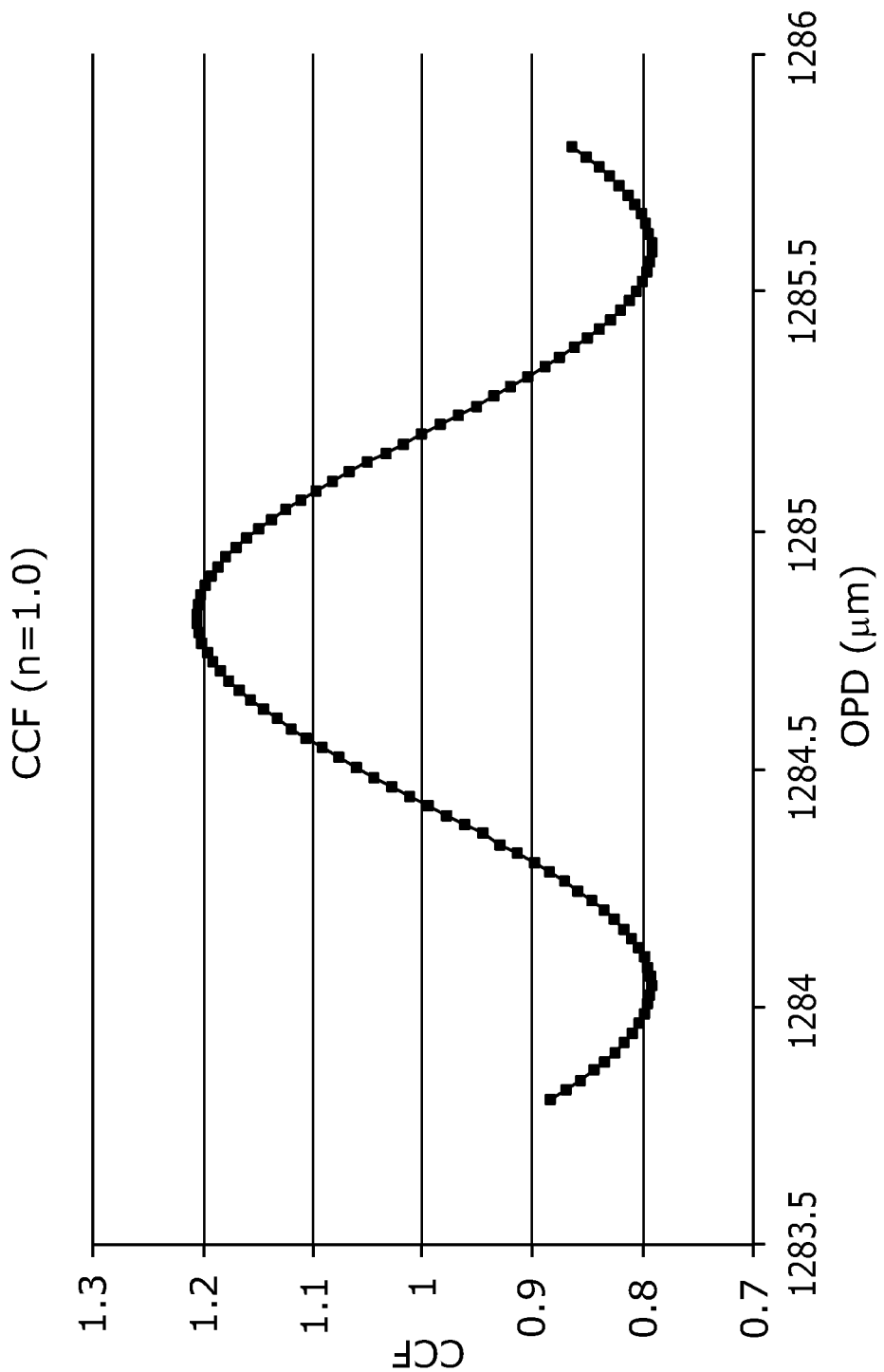
FIG. 8 is a magnification of part of the graph of FIG. 6.

It may be noted that whereas the total number of independent data points in the output of the described fast Fourier transform is limited to the number of points in the interference spectrum, a much larger number of data points can be provided in the output of the cross correlation function by increasing the density or number of periodic transfer functions used. This is illustrated in FIG. 8 which shows a small part of the cross correlation function of FIG. 6 in the region of the peak corresponding to the base optical cavity. In this case the optical path difference spacing was 10 nm.

As mentioned above, the one or more optical cavities may be used to measure various parameters at the sensor head 10 such as temperature and pressure through response of the interrogator to optical path difference of one or more optical cavities at the sensor head 10. Referring again to FIG. 4, for example, the position of the central peak which represents the strength of interference due to the pressure sensing cavity 36 of FIG. 2 will shift slightly to the left and right, depending on the movement of the diaphragm and the consequent optical path difference of this cavity. Using suitable analysis such as curve fitting to the peak this movement can be accurately tracked and used by the analyser 26 to provide a determination of pressure, changes in pressure or similar, subject to suitable calibration. Similarly, the position and movement of either of the other two peaks may be used by the analyser to provide a determination of temperature and/or changes in temperature at the sensor head 10. Referring to FIGS. 6, 7 and 8, the position and movement of any of the corresponding cross correlation function envelope peaks can be used by the analyser in a similar way to provide determinations of temperature, pressure and other parameters to which optical path difference at the sensor head is sensitive. However, in the case of the cross correlation function, and as illustrated in FIG. 8, it is possible to track a fine single cross correlation peak with a high degree of accuracy. Patent application GB1204673.6, subsequent corresponding applications and their publications, which are hereby incorporated by reference, describe how an optical path difference for determining a parameter at the sensor head may be derived by generating a course optical path difference signal using a Fourier transform or similar, and then refining this estimate using a cross correlation function.

It is important to note that generation by the analyser 26 of an indication of a liquid to be sensed as described above is based on strength of interference due to a particular optical cavity, whereas generation of indications of other parameters such as pressure and temperature at the sensor head 10 are based on changes in optical path difference of one or more of the optical cavities. As a result, the interrogator 20 may carry out both types of measurement simultaneously, for example based on the same interference spectrum generated by the spectral engine 30.

Figure 9:
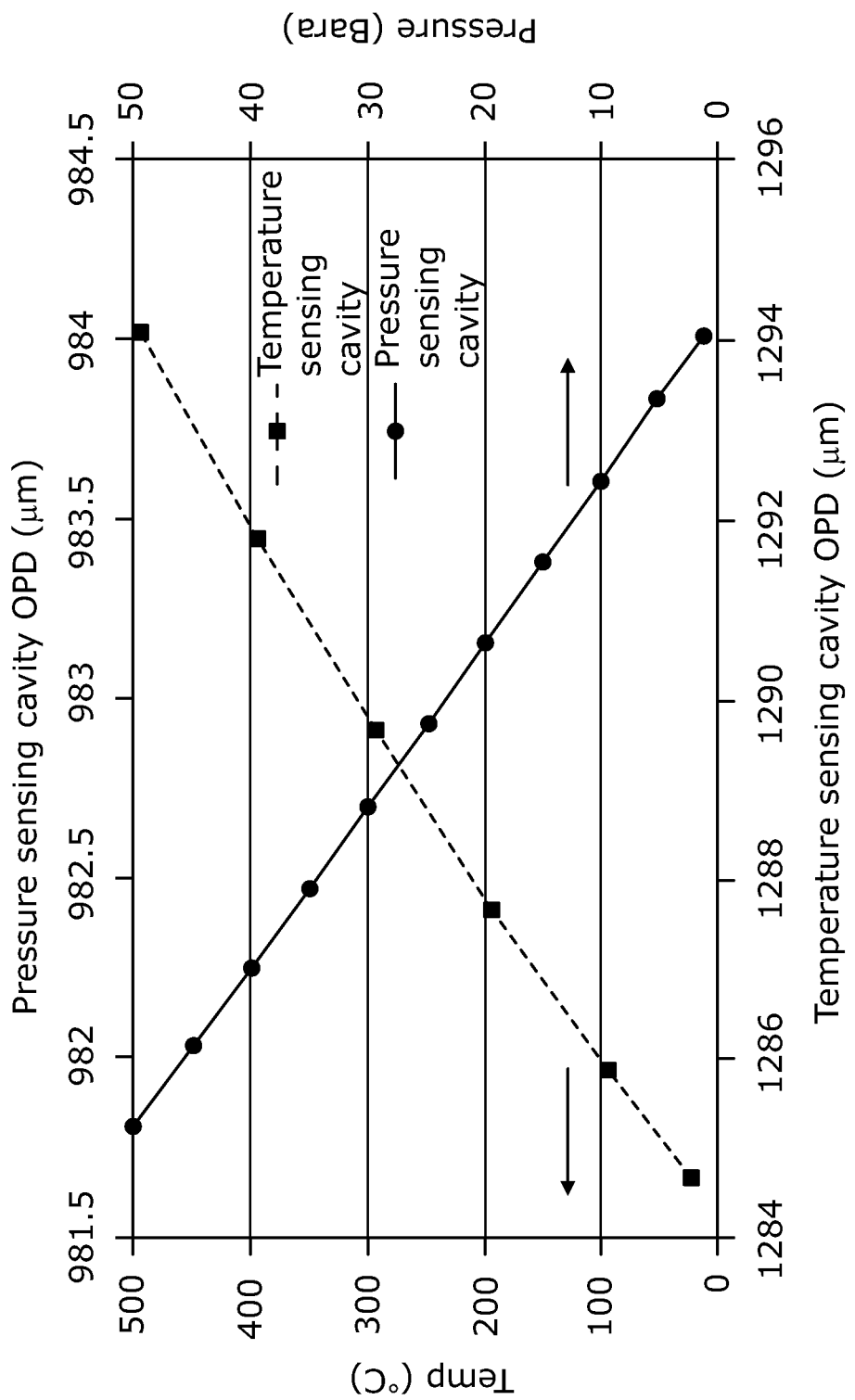
FIG. 9 shows calibration of pressure and temperature against optical path differences of pressure and temperature sensing cavities in the sensor head of FIG. 2.

FIG. 9 is a graph showing experimentally measured calibrations of the sensor head 10 of FIG. 2 having the dimensions and properties discussed above in respect of FIG. 3. In particular, the optical path difference of the pressure sensing optical cavity determined from a detection of the position of the corresponding (central) peak illustrated in FIGS. 6 and 7 and shown in the upper horizontal scale is plotted as the solid line against a calibration pressure applied to the sensor head 10 and shown in the right hand vertical scale. The optical path difference of the base optical cavity (right hand) peak illustrated in FIGS. 6 and 7 and shown in the lower horizontal scale is plotted as a broken line against a calibration temperature applied to the sensor head 10 and shown in the left hand vertical scale. Calibration curves such as those plotted in FIG. 9 may be used by the analyser 26 to generate and output indications of parameters at the sensor head such as temperature and pressure.

Referring to FIG. 9, it will be appreciated that by appropriately modifying the diameter and thickness of the diaphragm of the first optical cavity 12 of FIG. 2, the resulting deflection range can be adjusted to suit different ranges of pressure to be measured. For example, to suit relatively small changes and low pressures found in applications such as pressure measurement in aircraft fuel tanks a thinner and larger diameter diaphragm could be used, and the material used for the diaphragm could be varied. For example, replacing the sapphire material discussed above with a silica glass material, keeping physical dimensions unchanged, would increase the sensitivity to pressure of deflection of the diaphragm by about six times (the Young's modulus of sapphire being about 435 GPa, and of silica glass being in the region of 73 GPa).

Figure 10:
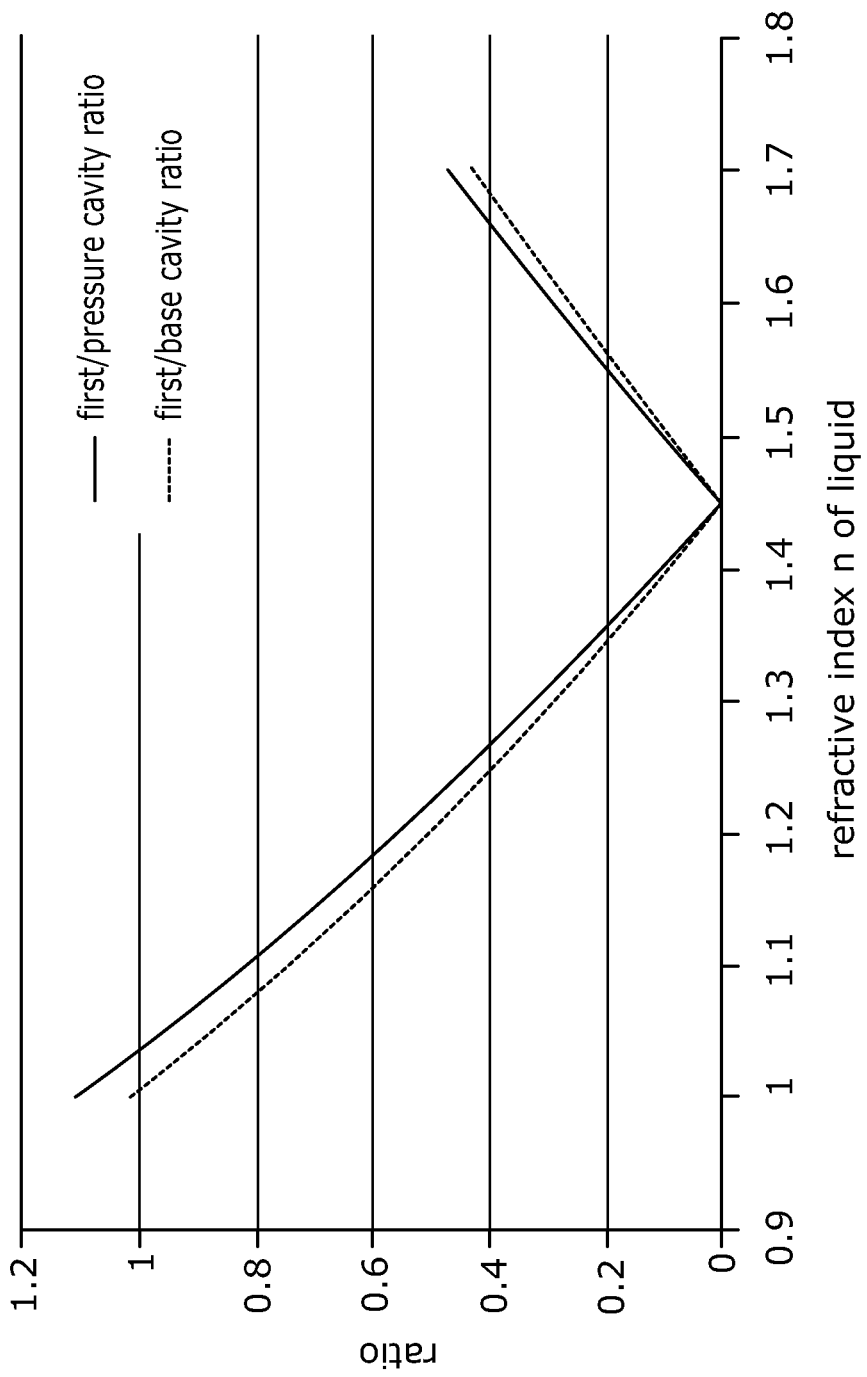
FIG. 10 is similar to FIG. 5 when a silica glass is used for the first optical cavity in place of sapphire.

Replacing the sapphire material (refractive index 1.76) of the first optical cavity 12 (which forms the diaphragm in FIG. 2) discussed above with a silica glass having a refractive index of 1.45 reduces the reflectivity at the optical boundary from about 7.5% to about 3.4%, and the relationship between interference strength due to the first optical cavity and refractive index of the gas or liquid in contact with the optical boundary previously shown in FIG. 5 also changes. FIG. 10 corresponds to FIG. 5, but with the first optical cavity formed of glass as proposed, and omitting the height of the peak for the first optical cavity shown in FIG. 4. In particular, the solid curve shows the ratio of the heights of the peaks in the fast Fourier transform based optical path difference signal between the first optical cavity 12 and the pressure optical cavity 36 of FIG. 2, and the broken curve shows this ratio between the first optical cavity 12 and the base optical cavity 34. A cusp is evident at a refractive index of the liquid of 1.45, which matches the refractive index of the glass first optical cavity so that no internal reflection takes place. Notably, it is still straightforward to distinguish between water with a refractive index of 1.33 and aviation fuel with a refractive index in the range 1.4 to 1.5 using this arrangement.

If temperature at the sensor head 10 is to be determined from the optical path difference of the first optical cavity then it is important for there to be sufficient reflection of the probe light at the optical boundary 14 over the full range of refractive index of gases and liquids which may be in contact at the optical boundary. FIG. 10 shows that temperature measurement using the optical path difference of a glass material first optical cavity in contact with aviation fuel having a refractive index similar to the glass may not be appropriate. In this case, it may be desirable to use a first optical cavity of sapphire or some other material of relatively high refractive index such as silicon. An advantage of using the optical path difference of the first optical cavity to detect temperature at the sensor head 10 may be that the measured temperature responds more quickly to temperature changes in the liquid or at the sensor head than if an optical cavity not exposed by the sensor head 10 is used for this purpose.

Figure 11:
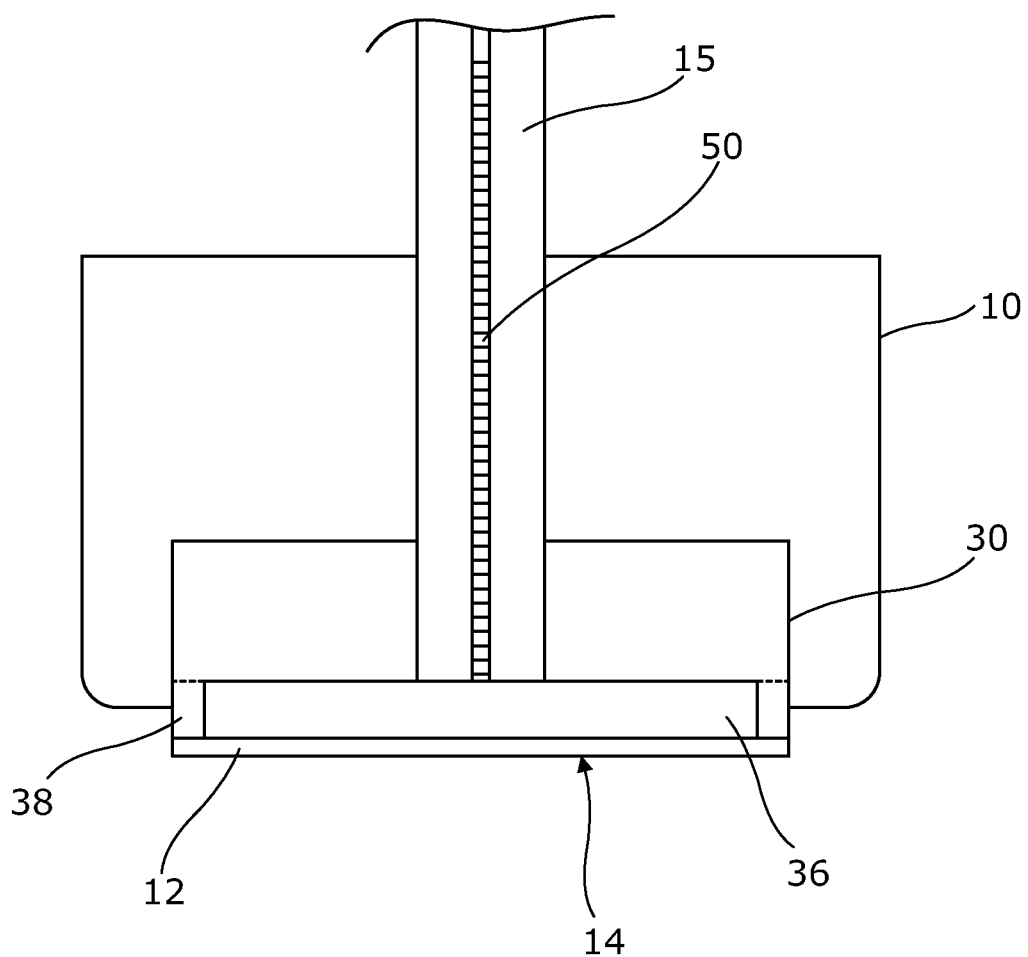
FIG. 11 shows an alternative structure for the sensor head of FIG. 2, in which a Bragg grating is incorporated into the optical fibre coupling the interrogator to the sensor head.

FIG. 11 illustrates in cross section an alternative construction for the sensor head 10. The sensing element 33 retains the optical boundary 14 for contact with a liquid to be sensed, the first optical cavity 12 and the pressure sensing optical cavity 36 shown in FIG. 2, but the optical fibre 15 is now modified to include a fibre Bragg grating (FBG) 50 in the core of the optical fibre 15, at least partly within or at least proximal to the sensor head 10 and/or the sensing element 33. A characteristic of the FBG, such as a reflection peak, changes with temperature of the optical fibre, and the interrogator 20 is then arranged to detect variations in temperature based on changes in this characteristic, with these temperature changes reflecting temperature changes at the sensor head 10. The FBG reflection peak at the Bragg wavelength typically shifts with temperature of the optical fibre at a rate of about 13 $\mu m/°$ C. at a probe light wavelength of 1550 nm, for example see the review of prior art relating to FBGs used in sensing applications found in Rao, Y-J., Meas. Sci. Technol., vol 8, 355-375 (1977).

Whereas in FIG. 2 the optical fibre 15 is optically coupled to the sensing element using an optical coupling 35 such as a micro-lens, in the arrangement of FIG. 11 the base optical cavity is no longer needed for detection of temperature at the sensor head 10 as this function can be carried out using the FBG, so the optical fibre 15 can be coupled more directly to the sensing element 33 for example by embedding into the sensing element 33 to provide good thermal contact between the sensing element and the FBG 50.

FIG. 11 shows the end of the optical fibre 15 having been cleaved, polished and/or otherwise treated, penetrating through the entire, depth of what in FIG. 2 formed the base optical cavity, with the end of the optical fibre providing one optical boundary of the pressure sensing optical cavity. The first optical cavity 12 may remain unchanged and can also be used for optical path difference temperature measurement if required.

Figure 12:
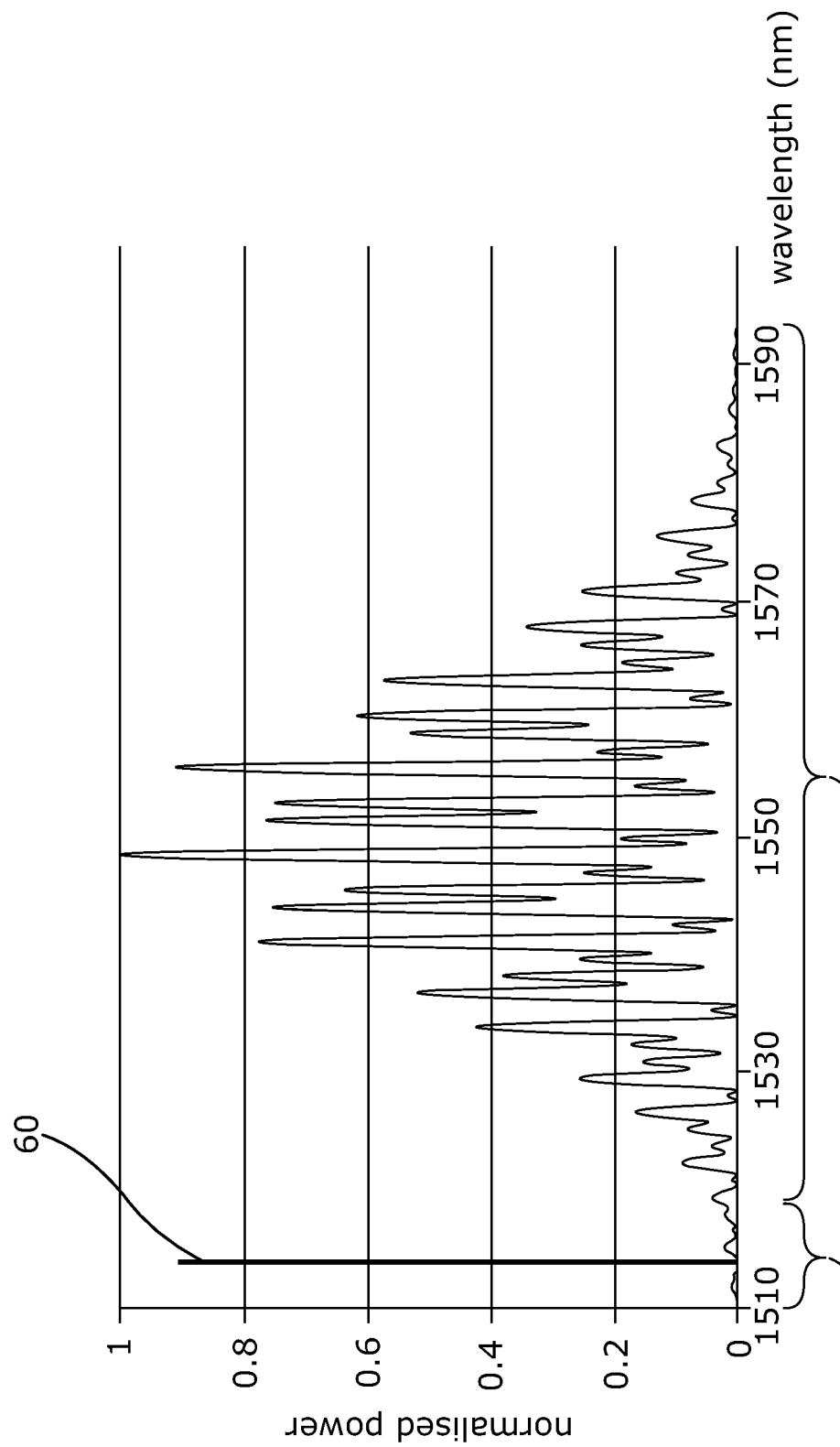
FIG. 12 shows the interference spectrum of FIG. 3 with interrogation of the Bragg grating of FIG. 11 accommodated in a marginal portion of the probe light spectrum.

The characteristic of the FBG 50 used for determining temperature can be detected using the detector 24 of FIG. 1, for example by detecting the Bragg wavelength as a peak 60 using the spectral engine 30, and using the analyser 26 to relate the Bragg wavelength to a detected temperature. However, care should be taken in designing the FBG 50 for an appropriate Bragg wavelength and reflection strength to avoid undue interference with other sensing functions based on the interference spectrum as described above. This can be achieved, for example, by selecting an FBG which is highly reflecting at a Bragg wavelength located towards the edge of the spectrum of the probe light as shown schematically in FIG. 12. High reflectivity can compensate for lower probe light intensity at the edge of the spectrum, which is then effectively divided into a marginal region 62 reserved for the measurement of the FBG characteristic, and a main region 64 used for detecting properties of interference arising from the Fabry-Perot optical cavities of the sensor head. To this end, the transform function 32 may omit the marginal region of the interference spectrum from the Fourier or other transform so as to avoid interference with the generation of a suitable optical path difference signal.

Although the embodiments described above are principally related to an optical sensor for sensing a liquid, the invention may be used in other circumstances, and more generally to detect reflectivity at the optical boundary 14. In one such example, the sensor may detect build up of a solid material on the optical boundary, which effects reflectivity at this boundary. For example, the sensor may be an optical sensor primarily for detecting one or more parameters such as temperature and pressure, but additionally be arranged as described above to detect build up of sooty deposits or similar if the sensor is installed in an engine such as a gas turbine or internal combustion engine, or in another dirty, or harsh environment. Such a sensor may also or instead detect degradation such as etching, or abrasion or other degradation of the optical boundary 14 which will also lead to a reduction in reflectivity at the boundary detectable using techniques described above.

In providing an indication of a liquid at the optical boundary, embodiments of the invention may be used for a variety of purposes other than in aviation fuel tanks. For example, the optical sensor may be arranged to detect liquids such as water remaining in a gas turbine or other engine after washing or a similar operation.

Various modifications may be made to the described embodiments without departing from the scope of the invention. For example, although the figures have illustrated a sensing element providing three Fabry Perot cavities which can be interrogated by the interrogator, just one, two or more Fabry Perot cavities can be used, and other types of optical cavities and optical elements giving rise to an interference signal in the probe light can be used as well as or instead of Fabry Perot cavities. In addition to detecting a liquid, temperature and pressure, other parameters may be detected at the sensor head, by suitable implementation of optical cavities. Detection of pressure at the sensor head may be manifested in various ways such as static and dynamic variations in pressure, as an acoustic signal or as information such as a spectral analysis of an acoustic signal at the sensor head. The optical sensor may combine two or more detected parameters in a single output, for example combining temperatures detected using two optical cavities to provide an average temperature or a temperature gradient.

The invention claimed is:

1. An optical sensor for sensing a liquid, comprising:
   a sensor head comprising one or more optical cavities, including a first optical cavity constructed as a Fabry-Perot cavity and comprising a solid material, the first optical cavity arranged such that a liquid to be sensed contacts the solid material at an external boundary of the first optical cavity;
   an optical source arranged to deliver probe light to the one or more optical cavities;
   a detector arranged to receive the probe light from the one or more optical cavities and to detect a magnitude of interference in the probe light caused by the first optical cavity, the magnitude of the interference being indicative of a refractive index of the liquid to be sensed; and
   an analyser arranged to generate an indication, based on the refractive index of the liquid to be sensed, of the liquid to be sensed at least in part by analyzing the magnitude of the detected interference caused by the first optical cavity.

2. The optical sensor of claim 1 wherein the one or more optical cavities includes one or more further optical cavities in addition to the first optical cavity, and the detector is arranged to detect separate interference in the received probe light caused by each of the further optical cavities.

3. The optical sensor of claim 2 wherein at least one of the further optical cavities is a pressure sensing cavity in the sensor head, and the analyser is arranged to generate an indication of pressure at the sensor head from an effect of changes in optical path difference of the pressure sensing cavity under changes in pressure on the detected interference in the received probe light caused by the pressure sensing cavity.

4. The optical sensor of claim 2 wherein at least one of the optical cavities is a temperature sensing optical cavity in the sensor head, and the analyser is arranged to generate an indication of temperature at the sensor head from an effect of changes in optical path difference of the temperature sensing optical cavity under changes in temperature on the detected interference in the received probe light caused by the temperature sensing optical cavity.

5. The optical sensor of claim 2 wherein the analyser is arranged to generate the indication of the sensed liquid based on relative magnitudes of the separate interference detected in the received probe light caused by two or more of the optical cavities respectively.

6. The optical sensor of claim 1 further comprising an optical fibre arranged to deliver the probe light to the sensor head, the optical fibre having formed therein proximal to the sensor head a Bragg grating, the optical sensor being arranged to detect variations in temperature at the sensor head from variations in a spectral characteristic of the Bragg grating.

7. The optical sensor of claim 6 wherein the optical sensor is arranged to detect variations in a characteristic of the Bragg grating using the probe light.

8. The optical sensor of claim 1 wherein the one or more optical cavities include a plurality of Fabry-Perot cavities.

9. The optical sensor of claim 1 wherein at least the first optical cavity is formed of one or more of sapphire, silica glass, and silicon.

10. The optical sensor of claim 1 wherein the detector comprises:
    a spectral engine arranged to detect in the received probe light an interference spectrum caused by the one or more optical cavities in the sensor head; and
    a transform function arranged to generate an optical path difference signal representing the magnitude of the detected interference for at least one or more optical path differences corresponding to the one or more optical cavities.

11. The optical sensor of claim 10 wherein the transform function is arranged to generate the optical path difference signal from the interference spectrum using at least one of a discrete Fourier transform and a cross-correlation of the interference spectrum with a set of periodic transfer functions.

12. The optical sensor of claim 10 wherein the magnitude of detected interference caused by any of the optical cavities is determined from a height of a corresponding peak in the optical path difference signal.

13. The optical sensor of claim 10 further arranged to detect, from the optical path difference signal, a measure of optical path difference of at least one of the one or more optical cavities, and to determine a parameter at the sensor head from the measure of optical path difference.

14. The optical sensor of claim 12 arranged to generate an indication of pressure at the sensor head from changes in optical path difference at a pressure sensing optical cavity of the sensor head, the changes in optical path difference being determined from the optical path difference signal.

15. The optical sensor of claim 12 arranged to generate an indication of temperature at the sensor head from changes in optical path difference at a temperature sensing optical cavity of the sensor head, the changes in optical path difference being determined from the optical path difference signal.

16. The optical sensor of claim 1 wherein the probe light comprises at least one of broadband light generated using one or more super-luminescent diodes and spread spectrum light generated using one or more tunable lasers.

17. The optical sensor of claim 1 wherein the sensor head is coupled to the optical source and the detector using an optical fibre carrying the probe light.

18. The optical sensor of claim 1 wherein the optical sensor is arranged to sense a refractive index of a liquid in contact with the optical boundary of the first optical cavity.

19. The optical sensor of claim 1 wherein the indication of the sensed liquid is an indication of a refractive index of the sensed liquid.

20. The optical sensor of claim 1 wherein the indication of the sensed liquid distinguishes between at least a first liquid and at least one other liquid or gas having a different refractive index to the first liquid at the boundary of the first optical cavity.

21. The optical sensor of claim 1, wherein the optical sensor is installed in a fuel tank of an aircraft fuel system.

22. The optical sensor of claim 21 wherein the indication of the sensed liquid, which the analyser is arranged to generate, distinguishes between water, fuel and gas at the boundary of the first optical cavity.

23. The optical sensor of claim 21 wherein the analyser is further arranged to generate an indication of at least one of temperature and pressure at the sensor head by interrogation of one or more of the optical cavities using the probe light.

24. The optical sensor of claim 1 wherein the analyser generates an indication of the presence or absence of the liquid to be sensed depending on the magnitude of the detected interference.

25. A method of sensing a liquid in contact with an external optical boundary, comprising:
providing a sensor head comprising one or more optical cavities including at least a first optical cavity constructed as Fabry-Perot cavity and comprising a solid material having the external optical boundary;
detecting reflection strength at the external optical boundary from a magnitude of interference caused by the first optical cavity in probe light delivered to and received back from the sensor head, the magnitude of the interference being indicative of a refractive index of the liquid to be sensed; and
generating an indication, based on the refractive index of the liquid, of the liquid to be sensed at least in part by analyzing the magnitude of the detected interference caused by the first optical cavity.

26. The method of claim 25 wherein the indication of the liquid to be sensed distinguishes between contact with the external optical boundary of a gas and a liquid, and/or between different liquids, by detection of a refractive index of liquid or gas in contact with the external optical boundary.

27. The method of claim 26 wherein the indication of the liquid to be sensed further distinguishes between contact with the external optical boundary of water and aviation fuel.

28. The method of claim 25, further comprising providing an analyser arranged to detect the reflection strength based on relative magnitudes of the detected interference in the received probe light caused by the first optical cavity and a further optical cavity of the one or more optical cavities.

29. The method of claim 25 wherein the one or more optical cavities include a plurality of Fabry Perot cavities.

30. The method of claim 25 wherein the magnitude of interference caused by the first optical cavity in probe light delivered to and received back from the sensor head is detected from a transform of an interference spectrum of the received probe light.

31. The method of claim 30 wherein the transform of the interference spectrum of the received probe light is at least one of a Fourier transform of the interference spectrum of the received probe light and a cross-correlation of the interference spectrum of the received probe light with a set of periodic transfer functions, and in either case corresponding to a range of optical path differences giving rise to the interference.

32. The method of claim 25 further comprising detecting pressure and/or temperature at the sensor head from interference caused by one or more of the one or more optical cavities.

* * * * *